United States Patent [19]

Spector

[11] Patent Number: 5,512,587
[45] Date of Patent: Apr. 30, 1996

[54] METHOD FOR TREATING OPIATE WITHDRAWAL

[76] Inventor: Sydney Spector, 600 Green Park, Nashville, Tenn. 37215

[21] Appl. No.: 359,060
[22] Filed: Dec. 19, 1994
[51] Int. Cl.$^6$ .................................................. A61K 31/425
[52] U.S. Cl. .................................................. 514/368
[58] Field of Search ............................................. 514/368

[56] References Cited

U.S. PATENT DOCUMENTS

| | | | |
|---|---|---|---|
| 3,709,868 | 1/1973 | Spector | 260/121 |
| 3,775,536 | 11/1973 | Spector et al. | |
| 3,822,245 | 7/1974 | Spector et al. | 260/112 |
| 4,042,682 | 8/1977 | Spector | 424/95 |
| 4,584,305 | 4/1986 | Brugmans | 514/368 |

OTHER PUBLICATIONS

Dougherty, et al. "Evidence of an immune system to brain communication axis that interferes with central opoid functions: Muramyl peptides attenuate opiate withdrawal." European Journal of Pharmacology, 141 (1987) 253–260.

Pompidou, et al. "Early Modifications of Lymphocytes Nuclear Refringence Phenomenon (NRP) Induced by Phythomagglutinin (PHA) and Isoprinosine in Allergy." European Journal of Rheumatology and Inflammation, vol. 1, (Nov. 3, 1978), 313–315.

Simone, et al. "Inosine Pranobex In The Treatment Of HIV Infection, A Review.", Intl. J. Immunopharmac, vol. 3, Suppl. 1, pp. 19–27, 1991.

Gordon, et al. "Isoprinosine and NPT 15392: Hypoxanthine-Containing Immunomodulators." (1988), pp. 535–553.

Dole, et al., "Methadone Maintenance Treatment—A Ten-Year Perspective." JAMA, May 10, 1976, vol. 235, No. 19, pp. 2117–2119.

Dole. "Implications of Methadone Maintenance for Theories of Narcotic Addiction." JAMA, 1988, vol. 260, No. 20, pp. 3025–3029.

Dole, et al. "Rehabilitation of the Street Addict." Arch. Envinron. Health, vol. 14, Mar., 1967, pp. 477–480.

Dole, et al., "Rehabilitation of Heroin Addicts After Blockade with Methadone." New York State Journal of Medicine, Aug., 1995 pp. 2011–2017.

Dole, et al. "Narcotic Blockade." Arch. Intern. Med. vol. 118, Oct., 1966, pp. 304–309.

Dole, et al., "The Use of Methadone for Narcotic Blockade." Br. J. Addict., 1968, vol. 63, pp. 55–57.

Primary Examiner—Raymond Henley, III
Assistant Examiner—Phyllis G. Spivack
Attorney, Agent, or Firm—James C. Weseman; Gray Cary Ware & Freidenrich

[57] ABSTRACT

A method is disclosed for treating opiate-addicted individuals to attenuate the withdrawal syndrome comprising administering the compound levamisole in a suitable pharmaceutical carrier.

3 Claims, No Drawings

METHOD FOR TREATING OPIATE WITHDRAWAL

BACKGROUND OF THE INVENTION

1. Field of the Invention

This invention relates to a composition and a method of using the composition for treating opiate-addicted individuals to attenuate the withdrawal syndrome.

2. Description of Related Art

Withdrawal from addiction to opiates is accompanied by a variety of metabolic and behavioral disorders including severe malaise, nausea, tremors, and cramps. At present, if one wants to attenuate or prevent the severity of withdrawal in a heroin addict, one administers methadone, which protects against withdrawal symptoms of opiate abstinence and blocks the euphorigenic action of heroin and other opiates. The problem with methadone is that it, too, is an addicting drug, and it must be administered daily (Dole, V. P. and Nyswander, M. E., Methadone Maintenance Treatment, a Ten-Year Perspective, *J. American Medical Association* 235(19):2117–2119 (1976). Levamisole is a compound which was originally used as an anthelminthic agent (*The Merck Index*, 11th Edition, Citation No. 9161). Recent interest in levamisole centers on the drug's restorative effects on suppressed immune response and anti-tumor activity, and the drug's effect on colorectal carcinoma (Burden et al., *Immunotherapy of Human Cancer*, Elsevier, North Holland, Inc., 1982, pp. 231–5). It would be desirable to have available for treating opiate addicts a nonaddictive compound that alleviates the severity of the withdrawal process and also has a positive effect on the immune system.

SUMMARY OF THE INVENTION

The present invention provides a composition and a method of treating opiate addicted individuals for opiate withdrawal which overcomes the above-mentioned problems. The claimed method comprises the step of administering to an opiate-addicted individual a treatment comprising levamisole or derivatives thereof in an amount sufficient to attenuate at least one manifestation of withdrawal syndrome. The claimed composition comprises levamisole in a suitable pharmaceutical carrier.

The above-discussed and many other features and attendant advantages of the present invention will become better understood by reference to the following detailed description of the invention.

DETAILED DESCRIPTION OF THE INVENTION

Certain advantages are provided by the composition and method of the present invention for protecting opiate addicts, upon abstaining from opiates, from the severity of withdrawal. These advantages include administering to the opiate addict a non-addictive substance and attenuating the severity of withdrawal symptoms. A further advantage of the claimed composition and its method of use is low toxicity. Another advantage is that the claimed composition can be administered orally.

Addicts for whom the claimed composition and method are useful include those addicted to narcotic agents such as, but not restricted to, opium alkaloid substances of morphine, heroin, codeine, methadone, meperidine (demerol) and levorphanol. In opiate addiction, with continued use of morphine there are liabilities associated with taking the drug, namely tolerance and physical dependence. Tolerance is a decrease in the effect of the drug with repeated use. The clinical consequence of opiate tolerance is the need to increase the dose of the drug during chronic administration in order to maintain the desired effects. Physical dependence is a change in functioning following repeated use, whereby further drug administration is necessary to avoid physiological disturbances.

The claimed method and composition for treating opiate withdrawal are based upon the discovery that a non-addictive substance, levamisole, administered to a subject resulted in an increase in the endogenous morphine content of the brain (Example 1, below). Accordingly, the claimed method of the invention comprises the step of administering to an opiate-addicted individual a treatment comprising levamisole or a derivative thereof. The amount of levamisole administered is sufficient to attenuate, that is to say, reduce or weaken at least one manifestation of the opiate withdrawal syndrome.

Behavioral changes during opiate withdrawal.

Naltrexone, an opiate receptor antagonist, was administered to opiate dependent rats, as described in the Examples below. The resulting opiate withdrawal or abstinence syndrome was quantitated by observing three behavioral signs: "wet-dog shakes," teeth chattering, and diarrhea. These behavior signs are described below.

Levamisole. Levamisole (The Merck Index, 11th Edition, Citation No. 9161), a synthetic phenylimidazothiazole, was originally used as an anthelminthic drug (*Journal of Immunology* 10:297 (1991)). Oncological interest in levamisole stems from reports demonstrating the drug's restorative effects on suppressed immune responses and antitumor activity in animal tumor models (Jansen, P. A., The Levamisole Story, *Prog. Drug Research* 20:347 (1976). While its mechanism of action is not known, reports suggest that levamisole may have immunomodulatory activity by increasing T-cell responses to mitogens and restoring suppressed cellular mediated hypersensitivity. Nonetheless, the effects of levamisole on monocyte and lymphocyte proliferation and cytotoxicity and other cytokine-induced cell surface soluble proteins are unknown. Levamisole has a low rate of severe or irreversible toxicity (Renoux, G., The General Immunopharmacology of Levamisole, *Drugs* 19:89–99 (1980); Moertel, C. G., et al. *N. Engl. J. Med.* 322:358 (1990)).

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to humans in a manner similar to other therapeutic agents. In general, the dosage required for therapeutic efficacy will range from about 1 to about 10 mg/kg, more usually 2 to 5 mg/kg of the host body weight. Alternatively, dosages within these ranges can be administered by constant infusion over an extended period of time, usually exceeding 24 hours, until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiological tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of about 0.1% to about 10%, preferably about 1% to about 10%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and contain about 0.1 to about 10% of active ingredient, preferably about 1% to about 10%.

Levamisole or derivatives and combinations thereof may be formulated into the compositions as neutral or salt forms. Pharmaceutically acceptable non-toxic salts include sodium, or hydrochloride acids, and the like.

The following examples are offered by way of illustration and are not intended to limit the invention in any manner.

Example 1

Effects of Levamisole on Endogenous Morphine Levels

A. Methods

Extractions of Morphine from Tissue. Brains removed from rats were homogenized in 10 mM HCl and then hydrolyzed. The tissues were then centrifuged at 10,000g for 30 minutes. The supernatant was adjusted to pH 8.5–9.0 and then subjected to organic extraction. Five volumes of 1:9 n-butanol in chloroform was added and shaken for 5 minutes. The organic phase was back-extracted into 2.0 to 2.5 ml of 10 mM HCl. The aqueous phase was evaporated to dryness.

The dried samples were reconstituted in 2 ml of 10 mM HCl plus 6 ml phosphate buffered saline pH 7.4, and the pH was adjusted to 8.9–9.0. The sample was passed through C-18 Sep-Pak cartridge (Millipore Corp., Edinburgh, N.C.) which had been activated with 5 ml methanol and flushed with 10 ml water. The sample was flushed with 7 ml of water and eluted with 7 ml of the mobile phase which contained water (95.5%), 1propanol (3%), pyridine (0.8%), and glacial acetic acid (0.3%). The eluate was then evaporated to dryness.

Quantification of Morphine in Tissue by High Pressure Liquid Chromatography (HPLC). An eluate obtained from the extraction procedure above was resuspended in 250 µl of mobile phase containing water (98.4%), 1-propanol (0.5%), pyridine (0.8%), glacial acetic acid (0.3%) pH5.2. The suspension was then filtered through 6.2 µm Z-Bind filter (Z Spin, Gelman Sciences Company, (Ann Arbor, Mich.), and injected into a Lichrosorb RP-18 10 µm column (250 mm) (Alltech, Deerfield, Ill.), flow rate 1.5 ml/min. 1-minute elution fractions were collected using a Foxy fraction collector (ISCO, Lincoln, Nebr.). The retention time for morphine was usually 8 minutes, and for codeine the retention time was 19 minutes. The eluate was then evaporated to dryness.

Radioimmunoassay. Morphine and codeine were detected in the tissues using radioimmunoassay. Samples were suspended in 200 µl of phosphate buffered saline, pH 7.4 plus 50 µl of morphine antibody and $I^{125}$ morphine and incubated for 90 minutes at 4° C. 250 µl of saturated ammonium sulfate was added and after 45 minutes the samples were filtered through GF/B glass fiber filters [Whatman Paper Corp, Gaithersburg, Md.) using a multichannel cell harvester (Brandell, Gaithersburg, Md.). Filters were counted in a gamma counter (LKB, Gaithersburg, MD), and concentrations of morphine and codeine determined using Riacole Software (LKB).

Preparation of Morphine Antibodies. Antibodies to morphine were prepared according to the methods disclosed in U.S. Pat. Nos. 3,709,868, 3,775,536, 3,822,245, and 4,042,682.

Qualitative and Quantitative High Performance Liquid Chromatographic Analysis of Other Monoamine Neurotransmitters and Metabolites in Brain Tissue Using Reductive Electrochemical Detection.

For analysis of brain tissue, dissected brain regions or micropunchs of specific nuclei from frozen sections (ranging from 0.05–20 mg) were homogenized for 2–3 s in 50–250 µL of ice-cold 0.025M perchloric acid (PCA) in a 1.5 mL microcentrifuge tube using a microtip sonic probe (Heat Systems Ultrasonics) at 10% power, 0.5 s impulse duration and 0.5 s interpulse interval. When homogenizing frozen brain tissue the tube was maintained at dry ice temperature until addition of the PCA and homogenization is carried out immediately to minimize thawing prior to disruption of the tissue. For tissue samples greater than 20 mg, the PCA volume is increased proportionately. If tissue concentrations of the target was to be calculated on the basis of weight, the tissue was weighed after dissection. Alternatively, where small sample size makes weighing impractible, a precise aliquot of the homogenate was removed for protein analysis. In order to permit replicate analysis of very small volumes of homogenate, the aliquot was first solubilized in 300 µL of 0.1N NaOH, mixed thoroughly and triplicate 100 µL portions of the mixture were analyzed for protein concentration by the method of Lowry et al. (64). The remaining brain homogenate was immediately centrifuged (12000×g for 10 min at 0°–4° C.) and the clear supernatant was carefully transferred to a clean microcentrifuge tube. A precise volume of supernatant was mixed with 2 to 10 times its volume of mobile phase A and a portion of the mixture was transferred to a 300 µL microinjection insert for HPLC analysis. We had found that tissue samples prepared in this matter remained in the autoinjector at 0°–4° C. for up to 18 h without significant loss of NE or 5-HT.

The HPLC system consisted of a Waters 510 HPLC pump (Milford, Mass., U.S.A.), a WISP 712 refrigerated autoinjector, an 8 mm×10 cm Nova Pack $C_{18}$ Radical Compression cartridge installed in a Waters RCM-100 radial compression module, an ESA model 5100 Coulochem electrochemical detector system consisting of a model 5021 conditioning Physics 4270 integrator. The detector sequence was set to operate in a screening mode for reductive detection as follows: The 5021 conditioning cell is set at +0.65 V in order to completely oxidize all readily oxidizable compounds in the effluent. The first electrode in the 5011 cell was set near the null point of the oxidative/reductive hydrodynamic voltammogram for the target compound (+0.10 V). This setting leaves the monoamines and their metabolites in the oxidized state but serves to reduce any compounds in the effluent stream that were more easily reducible than the target species. The third electrode in the series was set at the reductive potential sufficient to maximally reduce the target molecules in the effluent (either −0.30 or −0.20 V, see below). The output signal from the third electrode was linearly amplified by the 5100 controller and relayed to the integrator.

This detector array also can be used to obtain qualitative information about the identity and purity of the target peaks obtained from tissue samples. Under reproducible conditions, (i.e., identical mobile phase, temperature, detector cells, etc.) the voltammogram that results from analysis of a fixed amount of a specific compound was reproducible and was determined by the electronic characteristics of the compound, i.e., its structure. These curves may be similar for compounds that were closely related structurally, but varied significantly when the molecular structure was substantially different. Therefore, the peak heights produced when a precise amount of a compound was analyzed at reductive potentials between the settings needed to produced minimum and maximum peak heights were a reproducible characteristic of that compound. A qualitative check was performed as follows; authentic standards in molar amounts that yielded peak heights similar to the unknown peak(s) being checked were analyzed at three reductive potentials between the null point and the maximum setting (usually −0.25, −0.20, and −0.15 V) and the ratios of the peak heights at the different settings were calculated. The tissue sample was then analyzed using identical conditions, the peak height ratios for the target compounds at the different voltage settings were calculated and compared to those from the authentic standards. The mobile phase and column system described had been shown to resolve all of the most likely contaminating structural analogs of the target compounds that would have similar hydrodynamic voltammograms. If a target peak in the chromatogram was not the assumed compound, or more importantly, if it is contaminated to any significant degree by an otherwise undetectable co-eluting unknown, it was likely that the resulting peak height ratios will differ significantly from the standard's ratios. Therefore, the probability that contamination of a target peak by an unknown substance would remain undetected because the contaminant had both the identical elution time and a nearly identical voltammogram profile as the target compound was significantly reduced.

Alternatively, it was possible to operate the 5011 analytical cell to provide a qualitative check of all tissue analyses. In this mode the first electrode in the 5011 cell is set at an intermediary potential between the null voltage and the second 5011 electrode immediately prior to analysis by serial dilution with mobile phase A. A fraction of the compound, depending on the voltammogram shape, was reduced at the first electrode and a second fraction was reduced at the second electrode. As above, the ratios can be compared to the ratios obtained from analysis of authentic standards and serves to significantly increase the confidence of the qualitative identity and purity of tissue-derived peaks. However, because the detection of the compound was split between two electrodes, the minimum sensitivity of the assay is reduced accordingly and two simultaneous data acquisition channels are required.

Because of the screening capabilities of this detector array, the analytical electrode did not detect any compounds that did not undergo reversible oxidation/reduction and will detect only those reducible substances that reduce between +0.1 and −0.30 (or −0.20) V. This resulted in a minimum number of tissue-derived peaks that potentially could interfere with the analysis of neurotransmitters and/or metabolites.

All of the compounds of interest could be separated in 18 min using mobile phase A, which was prepared by dissolving 12.5 g citric acid, 40 mg heptane sulfonic acid, 30 mg disodium EDTA and 130 mL methanol in 1 L of water, and adjusting to pH 4.65 with 10N NaOH. The solution was vacuumed filtered through a 0.44 m nylon filter prior to use. All reagents were HPLC grade and freshly prepared 18 megohm organic-free water obtained from a Millipore Milli-R/O unit coupled to a 5 cartridge Milli-Q water system was used. The mobile phase, which has a starting detector current of −0.08 to 0.12 A at the −0.30 V setting, was recycled and replaced every 7–10 days, when the detector current increased above 0.20 A or when baseline noise of the detector output became unacceptable (>0.5 nA full scale). Normally, 50–100 samples can be run per liter of mobile phase without degradation of baseline stability or unacceptably increasing the detector current.

The oxidized form of NE, as well as DA and MHPG, were among the most easily reduced of the monoamines and their metabolites; maximum detector response is obtained at −0.20 to −0.22 V. The use of a lower reductive detector setting (−0.20 Volts vs −0.30 V for routine analysis) further improves the signal to noise ratio by reducing baseline noise and the number and/or magnitude of other potentially interfering peaks. This permits higher absolute sensitivity to be employed (1 m76 vs 7.0 nA full scale at −0.30 and −0.20 V, respectively) in the NE-specific assay. A similar strategy can be employed to increase the minimum sensitivity for analysis of low levels of DA and/or MHPG using mobile phase A, but at the expense of simultaneously measuring less easily reducible compounds such as 5-hydroxyindoleacetic acid (5-HIAA), 3-methoxytryramine (3-MT), 3,4-dihydroxphenylacetic acid (DOPAC) and homavanillic acid (HVA).

For quantitation, the peak height ratios of precise known amounts of authentic external standards and the corresponding peaks obtained following injection of precise volumes of the tissue samples were compared automatically by the integrator and the tissue concentrations were reported directly. In all cases the detector response was found to be linear, i.e., correlation for linear regression analysis >0.98, between the minimum detectable amount and 10 mg injected on column (data not presented). In order to compensate for possible changes in peak heights resulting from time-dependent change in the mobile phase, HPLC column efficiency, absolute detector sensitivity, ambient temperatures, or other variables which might occur during extended automatic analysis, the integrator was automatically re-calibrated with the external standard mixture every 4–6 tissue samples. The absolute concentration of standards in the calibration mixture is adjusted so that the concentrations in the standard and tissue injections are within a 10-fold range. Concentrated authentic standards (10 nmol/µL) were dissolved in water, were stored at −70° C. and replaced every 90 days. The actual calibration standards were prepared immediately prior to analysis by serial dilution with phase A. B. Administration of Morphine As shown in Table 1, Levamisole (35 mg/kg) administered to rats elevated the endogenous levels of morphine (pmoles/gm tissue) in the rat brain. Levamisole administration also caused elevation in codeine in various brain regions, although not to the same extent as morphine (Table 2) and also modified dopamine content in certain brain regions (Tables 3–6).

Levamisole was obtained from Sigma Chemical Co., St. Louis, Mo. The clinical characteristics of levamisole as reported in the literature (e.g. Jansen, P. A., *Prog. Drug. Res.* 20:347 (1976)) typically suggest that further studies are necessary to identify the mechanism of levamisole's antitumor activity. In contrast, the present invention is based upon the finding that levamisole has a profound effect in elevating the endogenous morphine and codeine content in tissues of mammals addicted to opiates, as set forth in Tables 1 and 2 below, which attenuates manifestations of the withdrawal syndrome (Table 7).

one can obtain an indication of the turnover of dopamine. The hypothalamus (Table 5), by way of example, had an increased turnover of dopamine. The hypothalamus also showed an increased level of endogenous morphine (Table 1). In the striatum (Table 4), the ratio of HVA:DA was reduced, indicating a reduced release of dopamine. The results in Tables 2–5 were subjected to the student t-test.

TABLE 1

EFFECT OF LEVAMISOLE (35 mg/kg i.p.) ON MORPHINE
CONTENT IN VARIOUS BRAIN REGIONS
PMOLES/G

| Time (min) | N | Cortex | Cerebellum | Hippocampus | Hypothalmus | Brainstem | Mid Brian | Striatum |
|---|---|---|---|---|---|---|---|---|
| 0 | 4 | 0.213 ± 0.025 | 0.138 ± 0.16 | 0.355 ± 0.03 | 0.235 ± 0.19 | 0.220 ± 0.01 | 0.390 ± 0.034 | 0.463 ± 0.03 |
| 15 | 4 | 0.303 ± 0.05 | 0.120 ± 0.02 | 0.840 ± 0.06* | 1.215 ± 0.03* | 0.530 ± 0.03* | 0.390 ± 0.020 | 0.715 ± 0.06* |
| 30 | 4 | 0.293 ± 0.035 | 0.180 ± 0.02 | 1.270 ± 0.05* | 3.115 ± 0.14* | 0.550 ± 0.04* | 0.505 ± 0.05 | 0.815 ± 0.04* |
| 60 | 4 | 0.255 ± 0.030 | 0.170 ± 0.15 | 1.117 ± 0.06* | 2.643 ± 0.07* | 0.540 ± 0.04* | 0.440 ± 0.026 | 0.527 ± 0.02 |
| 120 | 4 | 0.383 ± 0.028 | 0.307 ± 0.02* | 1.280 ± 0.06* | 2,540 ± 0.11* | 0.910 ± 0.03* | 0.350 ± 0.04 | 0.550 ± 0.04 |

\* = $P < 0.05$
Values represent mean ± S.E.M.
N = number of determinations

Example 2

Effects of Levamisole on Neutransmitters and Metabolites in Various Brain Areas

Rats were administered levamisole (35 mg/kg intraperitoneally). The effects of levamisole on neurotransmitters and their metabolites in various brain areas is presented in Tables 3–6. Six animals were used to generate the data for each time point. From the ratio of metabolite (dihydroxyphenylacetic acid (DOPAC) or homovanillic acid (HVA)) to dopamine,

TABLE 2

EFFECT OF LEVAMISOLE (35 mg/kg i.p.) ON CODEINE
CONTENT IN VARIOUS BRAIN REGIONS
PMOLES/G

| Time (min) | N | Cortex | Cerebellum | Hippocampus | Hypothalmus | Brainstem | Mid Brian | Striatum |
|---|---|---|---|---|---|---|---|---|
| 0 | 4 | 0.128 ± 0.02 | 0.130 ± 0.01 | 0.168 ± 0.02 | 0.103 ± 0.01 | 0.110 ± 0.01 | 0.200 ± 0.03 | 0.295 ± 0.02 |
| 15 | 4 | 0.140 ± 0.04 | 0.125 ± 0.02 | 0.115 ± 0.02 | 0.115 ± 0.02 | 0.100 ± 0.02 | 0.115 ± 0.015 | 0.320 ± 0.04 |
| 30 | 4 | 0.380 ± 0.06* | 0.130 ± 0.01 | 0.150 ± 0.02 | 0.140 ± 0.02 | 0.150 ± 0.03 | 0.110 ± 0.010 | 0.275 ± 0.03 |
| 60 | 4 | 0.313 ± 0.06* | 0.250 ± 0.02* | 0.297 ± 0.03* | 0.387 ± 0.01* | 0.237 ± 0.02* | 0.200 ± 0.020 | 0.520 ± 0.04* |
| 120 | 4 | 0.307 ± 0.04* | 0.215 ± 0.02* | 0.210 ± 0.03* | 0.125 ± 0.02* | 0.125 ± 0.02* | 0.170 ± 0.030 | 0.470 ± 0.03 |

\* = $P < 0.05$
Values represent mean ± S.E.M.
N = number of determinations

TABLE 3

EFFECT OF LEVAMISOLE (35 mg/kg i.p.) ON REGIONAL
MONOAMINE TRANSMITTER METABOLISM FMOLES/MG TISSUE

| | Tissue Wt (mg) | NOREPI | MHPG | DOPAMINE | DOPAC | HVA | 5-HT | 5-HIAA |
|---|---|---|---|---|---|---|---|---|
| CORTEX | | | | | | | | |
| Control Mean SEM | 800.2 ± 15.8 | 1320.2 ± 14.1 | 38.5± 1.7 | 5680.5 ± 343.8 | 349.4 ± 24.4 | 222.5 ± 19.8 | 1520.7 ± 57.4 | 504.2 ± 38.2 |
| 15 min | 785.8 ± 13.9 | 1316.4 ± 78.1 | 57.8 ± 8.6 | 5864.0 ± 453.0 | 218.3 ±* 17.1 | 232.8 ± 20.7 | 1447.5 ± 78.8 | 402.1 ± 27.6 |
| 30 min | 771.0 ± | 1238.5 ± | 61.7 ± | 6583.7 ± | 203.0 ±* | 232.6 ± | 1405.5 ± | 522.2 ± |

TABLE 3-continued

EFFECT OF LEVAMISOLE (35 mg/kg i.p.) ON REGIONAL MONOAMINE TRANSMITTER METABOLISM FMOLES/MG TISSUE

| | Tissue Wt (mg) | NOREPI | MHPG | DOPAMINE | DOPAC | HVA | 5-HT | 5-HIAA |
|---|---|---|---|---|---|---|---|---|
| | 80.0 | 70.0 | 8.8 | 916.8 | 12.7 | 27.9 | 92.1 | 30.7 |
| 60 min | 840.0 ± 4.6 | 1193.0 ± 99.0 | 53.9 ± 4.2 | 5710.3 ± 463.3 | 188.9 ±* 16.2 | 173.2 ± 6.2 | 1364.1 ± | 520.3 ± 40.8 |
| 120 min | 813.3 ± 19.2 | 1192.2 ± 57.6 | 48.8 ± 2.9 | 5930.1 ± 195.8 | 197.5 ±* 10.5 | 134.6 ±* 9.0 | 1865.4 ± 219.6 | 556.0 ± 16.9 |
| | | | | HIPPOCAMPUS | | | | |
| Control Mean SEM | 103.8 ± 4.2 | 2908.0 ± 101.4 | 42.5 ± 3.2 | 340.6 ± 39.2 | 42.9 ± 3.7 | 0.0 ± 0.0 | 1668.8 ± 98.2 | 1262.4 ± 63.5 |
| 15 min | 102.5 ± 6.0 | 3112.2 ± 291.7 | 50.2 ± 4.4 | 682.4 ±* 99.9 | 50.1 ± 4.9 | 0.0 ± 0.0 | 1959.6 ± 133.1 | 1205.4 ± 30.4 |
| 30 min | 109.0 ± 11.9 | 2554.8 ± 272.7 | 45.0 ± 2.0 | 817.6 ±* 167.7 | 66.9 ±* 3.5 | 16.1 ± 16.1 | 2093.5 ± 154.4 | 1230.1 ± 96.8 |
| 60 min | 103.8 ± 3.4 | 2795.5 ± 94.5 | 39.3 ± 3.1 | 707.4 ±* 81.9 | 59.7 ± 5.9 | 0.0 ± 0.0 | 2335.7 ±* 77.7 | 1363.1 ± 28.7 |
| 120 min | 111.5 ± 1.9 | 2570.1 ± 159.8 | 373.5 ±* 2.8 | 6.6.5 ±* 78.0 | 59.1 ± 5.0 | 0.0 ± 0.0 | 2045.3 ± 66.8 | 1.397.8 ± 33.7 |

\* $p < 0.05$

TABLE 4

EFFECT OF LEVAMISOLE (35 mg/kg i.p.) ON REGIONAL MONOAMINE TRANSMITTER METABOLISM FMOLES/MG TISSUE

| | Tissue Wt (mg) | NOREPI | MHPG | DOPAMINE | DOPAC | HVA | 5-HT | 5-HIAA |
|---|---|---|---|---|---|---|---|---|
| | | | | BRAIN STEM | | | | |
| Control Mean SEM | 195.0 ± 5.7 | 4080.2 ± 252.5 | 131.7 ± 3.3 | 509.6 ± 17.7 | 98.2 ± 1.8 | 69.5 ± 5.4 | 3735.9 ± 108.9 | 1231.4 ± 63.4 |
| 15 min | 177.0 ± 5.3 | 3928.6 ± 151.0 | 187.1 ± 11.9 | 987.6 ±* 17.8 | 148.1 ± 5.4 | 123.4 ±* 6.6 | 3759.1 ± 186.2 | 1140.3 ± 51.5 |
| 30 min | 197.8 ± 7.5 | 3532.2 ± 165.6 | 174.6 ±* 13.7 | 1135.0 ±* 30.9 | 16.8 ±* 7.6 | 182.0 ±* 9.8 | 3773.3 ± 261.6 | 1382.0 ± 36.5 |
| 60 min | 194.5 ± 7.5 | 3932.5 ± 126.4 | 177.7 ±* 12.8 | 1046.1 ±* 45.2 | 146.9 ±* 6.7 | 162.0 ±* 11.9 | 4790.0 ±* 372.7 | 1449.5 ± 53.3 |
| 120 min | 186.5 ± 6.7 | 3950.8 ± 270.4 | 155.6 ± 16.5 | 1058.1 ±* 105.4 | 132.9 ±* 11.6 | 143.9 ±* 18.1 | | |
| | | | | CEREBELLUM | | | | |
| Control Mean SEM | 264.4 ± 5.6 | 1369.2 ± 25.0 | 152.4 ± 9.1 | 72.3 ± 8.9 | 32.3 ± 11.2 | 15.8 ± 9.8 | 303.8 ± 21.6 | 244.6 ± 15.4 |
| 15 min | 260.8 ± 4.3 | 1044.7 ±* 55.1 | 219.0 ± 22.4 | 206.6 ±* 24.1 | 30.9 ± 2.0 | 50.7 ± 4.0 | 287.1 ± 9.8 | 191.7 ± 19.5 |
| 30 min | 269.3 ± 1.8 | 1125.9 ± 124.6 | 225.9 ± 29.2 | 265.2 ±* 34.5 | 33.8 ± 2.0 | 108.6 ±* 11.7 | 296.2 ± 43.4 | 227.1 ± 20.8 |
| 60 min | 267.5 ± 4.3 | 1165.4 ± 43.3 | 212.0 ± 10.2 | 243.8 ±* 10.3 | 33.8 ± 2.0 | 98.1 ±* 11.8 | 297.2 ± 26.6 | 253.1 ± 17.9 |
| 120 min | 261.3 ± 6.2 | 1619.8 ± 334.5 | 296.9 ± 58.2 | 227.0 ±* 47.3 | 36.0 ± 7.9 | 110.0 ±* 34.3 | 319.1 ± 24.9 | 361.5 ± 126.4 |

\* = $P < 0.05$

TABLE 5

EFFECT OF LEVAMISOLE (35 mg/kg i.p.) ON REGIONAL MONOAMINE TRANSMITTER METABOLISM
FMOLES/MG TISSUE

|  | Tissue Wt (mg) | NOREPI | MHPG | DOPAMINE | DOPAC | HVA | 5-HT | 5-HIAA |
|---|---|---|---|---|---|---|---|---|
| STRIATUM | | | | | | | | |
| Control Mean SEM | 53.0 ± 4.6 | 833.2 ± 130.5 | 32.7 ± 5.8 | 118378.2 ± 6443.9 | 6973.8 ± 364.1 | 3973.0 ± 243.0 | 912.1 ± 63.6 | 4221.5 ± 212.7 |
| 15 min | 58.3 ± 1.2 | 794.9 ± 112.1 | 34.2 ± 1.2 | 137657.1 ± 7509.0 | 3838.7 ± 305.9 | 3650.6 ± 279.7 | 1090.3 ± 166.6 | 3490.5 ± 289.7 |
| 30 min | 62.0 ± 5.9 | 680.2 ± 99.3 | 42.2 ± 4.3 | 130092.9 ± 5028.1 | 2917.4 ±* 164.2 | 2465.4 ±* 279.2 | 11240.3 ± 55.3 | 3043.1 ± 401.0 |
| 60 min | 47.3 ± 5.8 | 1235.3 ± 133.8 | 40.4 ± 3.3 | 142572.0 ± 15373.4 | 3549.3 ±* 404.3 | 2430.6 ±* 197.4 | 1158.5 ± 72.2 | 3622.2 ± 465.8 |
| 120 min | 57.5 ± 3.11 | 975.2 ± 178.8 | 31.0 ± 4.0 | 125249.0 ± 5780.0 | 3348.1 ±* 400.5 | 1729.1 ± 214.5 | 1018.5 ± 115.4 | 3513.0 ± 276.4 |

* = $p < 0.05$

TABLE 6

EFFECT OF LEVAMISOLE (35 mg/kg i.p.) ON REGIONAL MONOAMINE TRANSMITTER METABOLISM
FMOLES/MG TISSUE

|  | Tissue Wt (mg) | NOREPI | MHPG | DOPAMINE | DOPAC | HVA | 5-HT | 5-HIAA |
|---|---|---|---|---|---|---|---|---|
| HYPOTHALAMUS | | | | | | | | |
| Control Mean SEM | 61.4 ± 3.0 | 10134.6 ± 513.8 | 34.6 ± 2.5 | 3035.4 ± 570.6 | 286.7 ± 10.4 | 21.2 ± 21.2 | 3466.7 ± 210.7 | 2456.9 ± 74.5 |
| 15 min | 58.8 ± 2.4 | 10421.5 ± 417.0 | 53.4 ±* 4.7 | 6421.4 ± 496.0 | 317.9 ± 28.8 | 86.1 ± 37.2 | 4122.7 ± 219.7 | 2149.2 ± 163.9 |
| 30 min | 71.8 ± 3.3 | 9950.0 ± 1280.1 | 61.6 ±* 2.3 | 8451.2 ±* 302.0 | 470.8 ±* 18.0 | 207.7 ±* 27.2 | 4702.3 ±* 397.1 | 2151.0 ± 98.8 |
| 60 min | 66.5 ± 4.6 | 9659.9 ± 692.2 | 43.4 ± 3.6 | 6145.3 ± 350.2 | 352.5 ± 20.4 | 129.4 ± 16.6 | 4633.4 ±* 187.8 | 2168.7 ± 76.4 |
| 120 min | 60.5 ± 2.9 | 9799.9 ± 478.6 | 39.1 ± 5.1 | 6247.3 ± 327.3 | 321.2 ± 25.3 | 90.1 ±* 4.70 | 4611.2 ±* 127.0 | 2491.6 ± 62.9 |
| MID BRAIN | | | | | | | | |
| Control Mean SEM | 207.0 ± 11.1 | 3570.5 ± 120.1 | 29.8 ± 0.8 | 2653.6 ± 191.0 | 261.1 ± 11.7 | 157.9 ± 4.9 | 3784.3 ± 242.4 | 2117.0 ± 120.7 |
| 15 min | 223.0 ± 8.4 | 3328.3 ± 326.3 | 43.3 ±* 2.8 | 5584.5 ±* 695.4 | 246.7 ± 23.5 | 213.1 ± 15.2 | 3959.4 ± 160.4 | 1752.1 ±* 51.4 |
| 30 min | 188.5 ± 11.3 | 2652.8 ± 77.5 | 38.6 ± 3.8 | 4171.2 ± 511.1 | 203.2 ± 12.2 | 164.9 ± 15.8 | 3963.5 ± 153.0 | 2133.3 ± 75.8 |
| 60 min | 187.5 ± 9.1 | 3230.8 ± 168.5 | 32.9 ± 0.7 | 5375.9 ± 1290.9 | 253.3 ± 38.2 | 195.4 ± 27.3 | 4625.7 ± 104.5 | 2456.4 ± 58.0 |
| 120 min | 200.5 ± 9.1 | 3269.3 ± 135.2 | 26.9 ± 372.2 | 3749.0 ± 17.5 | 221.0 ± 12.6 | 150.2 ± 532.3 | 5468.2 ±* 77.4 | 2687.9 ± |

* = $p < 0.05$

Example 3

Effect of Levamisole on Opiate-Addicted Rats

The attenuation of withdrawal symptoms in opiate-addicted rats was demonstrated by administering the claimed treatment and composition of levamisole to morphine-addicted rats.

Preparation of Opiate Addicted Rats. The following protocol was used to develop opiate-addicted rats which would undergo subsequent opiate withdrawal manifestations. Rats were injected with morphine sulfate (5 mg/kg i.p.) twice a day, at 10 am and at 3 pm for two consecutive days. On the third day, morphine sulfate (5 mg/kg i.p.) was administered at 10 am. The rats were divided into two groups. In group one, levamisole was administered 2.5 hours later. One hour after levamisole administration, the animals in group one were given naltrexone (3 mg/kg i.p.), which, in the absence of levamisole, precipitates opiate withdrawal and unattenuated concomitant behavioral manifestations of opiate withdrawal. In the second group, naltrexone was administered following the morphine treatment. In this second group, withdrawal or abstinence from opiate addiction was precipitated by the antagonist naltrexone. The withdrawal syndrome was observed and quantitated by three behavioral signs: wet dog shakes, teeth chattering, and diarrhea.

a. Wet dog shakes. This behavior pattern mimics that seen when a dog's head is wet, and the animal tires to shake the water off. Normally, rats do not exhibit wet dog shakes, but during the withdrawal syndrome, it becomes a prominent sign and one counts within a 10 minute period the number of times the rat shows this behavior.

b. Teeth chattering. Again, rats normally do not exhibit teeth chattering. However, during withdrawal this is a readily observable sign to monitor.

c. Fecal boli. In contrast to normal fecal boli that rats defecate, during withdrawal, with or without naltrexone, they have diarrhea and their underbelly becomes matted with feces.

Administration of Levamisole. Table 6 shows that levamisole attenuated the behavioral effects of withdrawal in morphine-addicted rats. In particular, Table 6 shows that the claimed composition and method for treating opiate withdrawal attenuated or reduced the severity of wet dog shakes, teeth chattering. Levamisole prevented the diarrhea, and the rats excreted discrete fecal boli, which were countable. The rats' levels of endogenous morphine was likewise elevated by levamisole treatment, as indicated in Table 1.

TABLE 7

EFFECT OF LEVAMISOLE (34 mg/kg i.p.) ON OPIATE WITHDRAWAL SYNDROME

| TREATMENT | N | WET DOG SHAKES | TEETH CHAT- TERING | FECAL BOLI |
|---|---|---|---|---|
| Placebo + Naltrexone | 4 | 0 | 0 | 8 ± 2 |
| Morphine + Naltrexone | 4 | 8 ± 1* | 7 ± 1* | Diarrhea* |
| Morphine + Levamisole + Naltrexone | 4 | 3 ± 1** | 3 ± 1** | 5 ± 2** |
| Placebo + Levamisole + Naltrexone | 4 | 0 | 0 | 7 ± 2 |

N = number of rats/gp

Numbers represent mean ± S.E.M. of the times the rats exhibited the behavioral signs during the 10 min. observation period.
**Placebo + Naltrexone vs. morphine + Naltrexone $P < 0.05$
**Morphine + Nalatrexone vs. morphine + Levamisole + Naltrexone $p < 0.05$.

The findings of Table 7 in view of the claimed composition's elevation of the endogenous opiate alkaloids morphine and codeine indicates that the claimed composition and method are useful for treating human opiate addicts as levamisole, like methadone, blocks withdrawal symptoms, and would extend as well to the typical action of methadone for the treatment of opiate addicts, which includes the prevention of "drug hunger" and the blockade of the euphoric effects of any illicit self-administered narcotics by the phenomenon of opiate cross tolerance.

Having thus described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for treating opiate withdrawal comprising the step of administering to an opiate-addicted individual a treatment comprising levamisole in an amount sufficient to attenuate at least one manifestation of the withdrawal syndrome.

2. The method of claim 1 wherein said opiate is selected from the group of opiates consisting of morphine, heroin, codeine, methadone, meperidine, and levorphanol.

3. The method of claim 1 wherein said amount of levamisole is from about 2 mg/kg to about 20 mg/kg of an individual's body weight.

* * * * *